(12) United States Patent
Metzger

(10) Patent No.: US 9,408,704 B2
(45) Date of Patent: Aug. 9, 2016

(54) REVISION KNEE TIBIAL LOCKING MECHANISM

(71) Applicant: Biomet Manufacturing, LLC, Warsaw, IN (US)

(72) Inventor: Robert Metzger, Wakarusa, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 14/143,546

(22) Filed: Dec. 30, 2013

(65) Prior Publication Data

US 2014/0114427 A1      Apr. 24, 2014

Related U.S. Application Data

(62) Division of application No. 13/162,789, filed on Jun. 17, 2011, now Pat. No. 8,617,250.

(51) Int. Cl.
    *A61F 2/38*      (2006.01)
    *A61F 2/30*      (2006.01)

(52) U.S. Cl.
    CPC .............. *A61F 2/389* (2013.01); *A61F 2/3868* (2013.01); *A61F 2002/3021* (2013.01); *A61F 2002/3054* (2013.01); *A61F 2002/3069* (2013.01); *A61F 2002/30171* (2013.01); *A61F 2002/30332* (2013.01); *A61F 2002/30365* (2013.01); *A61F 2002/30377* (2013.01); *A61F 2002/30481* (2013.01); *A61F 2002/30505* (2013.01); *A61F 2002/30563* (2013.01)

(58) Field of Classification Search
    CPC ................................ A61F 2/389; A61F 2/3859
    USPC .......... 623/20.26–20.29, 20.34, 20.32, 20.15, 623/20.14, 19.14
    See application file for complete search history.

(56) References Cited

U.S. PATENT DOCUMENTS

| | | | | |
|---|---|---|---|---|
| 3,996,624 A | * | 12/1976 | Noiles | 623/20.24 |
| 4,001,896 A | * | 1/1977 | Arkangel | 623/20.24 |
| 4,257,129 A | | 3/1981 | Volz | |
| 4,714,474 A | | 12/1987 | Brooks, Jr. et al. | |
| 4,731,087 A | | 3/1988 | Sculco et al. | |
| 4,936,853 A | | 6/1990 | Fabian et al. | |
| 4,938,769 A | | 7/1990 | Shaw | |
| 4,944,757 A | | 7/1990 | Martinez et al. | |
| 4,963,155 A | * | 10/1990 | Lazzeri et al. | 623/22.42 |
| 5,080,675 A | | 1/1992 | Lawes et al. | |
| 5,108,442 A | | 4/1992 | Smith | |
| 5,137,535 A | * | 8/1992 | Keller | 623/20.36 |

(Continued)

OTHER PUBLICATIONS

"U.S. Appl. No. 13/162,789, Non Final Office Action mailed Feb. 22, 2013", 10 pgs.

(Continued)

*Primary Examiner* — Alvin Stewart
(74) *Attorney, Agent, or Firm* — Schwegman Lundberg & Woessner, P.A.

(57) ABSTRACT

A tibial prosthesis assembly including a tibial component and a tibial insert. The tibial component includes an inferior bone engaging surface, a superior surface, and a first retention feature. The tibial insert includes an inferior tibial component engaging surface, a superior bearing surface, and a second retaining feature. The first and the second retaining features cooperate to mate the tibial insert with the tibial component at one of a plurality of fixed rotational orientations relative to the tibial component.

16 Claims, 5 Drawing Sheets

(56) References Cited

U.S. PATENT DOCUMENTS

| | | | | |
|---|---|---|---|---|
| 5,194,066 | A | 3/1993 | Van Zile | |
| 5,201,881 | A | 4/1993 | Evans | |
| 5,282,868 | A | 2/1994 | Bahler | |
| 5,330,534 | A * | 7/1994 | Herrington et al. | 623/20.27 |
| 5,344,460 | A | 9/1994 | Turanyi et al. | |
| 5,387,240 | A | 2/1995 | Pottenger et al. | |
| 5,413,608 | A | 5/1995 | Keller | |
| 5,549,686 | A * | 8/1996 | Johnson et al. | 623/20.27 |
| 5,653,764 | A * | 8/1997 | Murphy | 623/23.15 |
| 5,658,340 | A * | 8/1997 | Muller et al. | 623/19.14 |
| 5,702,457 | A * | 12/1997 | Walch et al. | 623/19.13 |
| 5,702,464 | A | 12/1997 | Lackey et al. | |
| 5,876,459 | A | 3/1999 | Powell | |
| 5,879,394 | A | 3/1999 | Ashby et al. | |
| 5,906,644 | A | 5/1999 | Powell | |
| 5,910,171 | A * | 6/1999 | Kummer et al. | 623/18.11 |
| 5,957,979 | A | 9/1999 | Beckman et al. | |
| 5,964,808 | A | 10/1999 | Blaha et al. | |
| 5,997,577 | A * | 12/1999 | Herrington et al. | 623/20.15 |
| 6,004,352 | A * | 12/1999 | Buni | 623/20.33 |
| 6,039,764 | A * | 3/2000 | Pottenger et al. | 623/20.32 |
| 6,053,945 | A * | 4/2000 | O'Neil et al. | 623/20.32 |
| 6,090,144 | A * | 7/2000 | Letot et al. | 623/20.34 |
| 6,126,692 | A | 10/2000 | Robie et al. | |
| 6,197,062 | B1 * | 3/2001 | Fenlin | 623/19.12 |
| 6,206,926 | B1 * | 3/2001 | Pappas | 623/20.27 |
| 6,210,444 | B1 * | 4/2001 | Webster et al. | 623/20.33 |
| 6,210,445 | B1 | 4/2001 | Zawadzki | |
| 6,217,618 | B1 * | 4/2001 | Hileman | 623/20.33 |
| 6,299,646 | B1 | 10/2001 | Chambat et al. | |
| 6,306,172 | B1 * | 10/2001 | O'Neil et al. | 623/20.15 |
| 6,319,283 | B1 * | 11/2001 | Insall et al. | 623/20.33 |
| 6,436,145 | B1 | 8/2002 | Miller | |
| 6,485,519 | B2 | 11/2002 | Meyers et al. | |
| 6,500,207 | B1 * | 12/2002 | Keller | 623/20.15 |
| 6,500,208 | B1 | 12/2002 | Metzger et al. | |
| 6,506,215 | B1 * | 1/2003 | Letot et al. | 623/20.29 |
| 6,569,203 | B1 * | 5/2003 | Keller | 623/23.47 |
| 6,589,282 | B2 * | 7/2003 | Pearl | 623/19.14 |
| 6,623,526 | B1 | 9/2003 | Lloyd | |
| 6,699,291 | B1 * | 3/2004 | Augoyard et al. | 623/20.27 |
| 6,709,461 | B2 | 3/2004 | O'Neil et al. | |
| 6,716,250 | B2 * | 4/2004 | Ganjianpour | 623/22.42 |
| 6,916,340 | B2 | 7/2005 | Metzger et al. | |
| 6,942,699 | B2 * | 9/2005 | Stone et al. | 623/19.14 |
| 6,974,483 | B2 * | 12/2005 | Murray | 623/22.42 |
| 6,986,791 | B1 * | 1/2006 | Metzger | 623/20.24 |
| 7,014,660 | B2 * | 3/2006 | Fenning et al. | 623/20.29 |
| 7,025,788 | B2 | 4/2006 | Metzger et al. | |
| 7,070,622 | B1 | 7/2006 | Brown et al. | |
| 7,094,259 | B2 | 8/2006 | Tarabichi | |
| 7,101,401 | B2 | 9/2006 | Brack | |
| 7,135,044 | B2 * | 11/2006 | Bassik et al. | 623/22.42 |
| 7,175,664 | B1 * | 2/2007 | Lakin | 623/19.14 |
| 7,175,666 | B2 | 2/2007 | Yao | |
| 7,338,529 | B1 * | 3/2008 | Higgins | 623/20.14 |
| 7,351,263 | B2 * | 4/2008 | Afriat | 623/20.27 |
| 7,422,605 | B2 | 9/2008 | Burstein et al. | |
| 7,740,662 | B2 * | 6/2010 | Barnett et al. | 623/20.33 |
| 7,766,969 | B2 | 8/2010 | Justin et al. | |
| 8,012,215 | B2 | 9/2011 | Metzger et al. | |
| 8,092,546 | B2 | 1/2012 | Coon et al. | |
| 8,105,386 | B2 * | 1/2012 | Perrone et al. | 623/20.29 |
| 8,105,387 | B2 * | 1/2012 | Barnett et al. | 623/20.32 |
| 8,152,853 | B2 | 4/2012 | Belcher | |
| 8,236,059 | B2 * | 8/2012 | Stone et al. | 623/19.14 |
| 8,366,781 | B2 | 2/2013 | Berelsman et al. | |
| 8,523,950 | B2 * | 9/2013 | Dees et al. | 623/20.28 |
| 8,617,250 | B2 | 12/2013 | Metzger | |
| 8,623,092 | B2 * | 1/2014 | Bickley et al. | 623/18.11 |
| 8,702,804 | B2 * | 4/2014 | Smith et al. | 623/20.35 |
| 8,894,715 | B2 * | 11/2014 | Metzger et al. | 623/20.31 |
| 8,936,648 | B2 * | 1/2015 | Collard et al. | 623/20.29 |
| 2001/0014827 | A1 | 8/2001 | Chambat et al. | |
| 2002/0072802 | A1 | 6/2002 | O'Neil et al. | |
| 2003/0009228 | A1 * | 1/2003 | Meyers et al. | 623/20.24 |
| 2003/0009229 | A1 * | 1/2003 | Pappas | 623/20.27 |
| 2003/0009232 | A1 * | 1/2003 | Metzger et al. | 623/20.29 |
| 2003/0093156 | A1 | 5/2003 | Metzger et al. | |
| 2003/0153980 | A1 | 8/2003 | Brack | |
| 2003/0195634 | A1 | 10/2003 | Fenning et al. | |
| 2003/0216809 | A1 * | 11/2003 | Ferguson | 623/13.14 |
| 2004/0002767 | A1 * | 1/2004 | Wyss | 623/20.27 |
| 2004/0054416 | A1 * | 3/2004 | Wyss et al. | 623/20.27 |
| 2004/0143335 | A1 * | 7/2004 | Dews et al. | 623/19.14 |
| 2004/0215345 | A1 * | 10/2004 | Perrone et al. | 623/20.32 |
| 2004/0225368 | A1 | 11/2004 | Plumet et al. | |
| 2005/0154472 | A1 * | 7/2005 | Afriat | 623/20.29 |
| 2005/0246027 | A1 | 11/2005 | Metzger et al. | |
| 2007/0043448 | A1 * | 2/2007 | Murray | 623/22.46 |
| 2007/0100463 | A1 * | 5/2007 | Aram et al. | 623/20.29 |
| 2007/0135924 | A1 * | 6/2007 | Verhoogen | 623/18.11 |
| 2007/0150065 | A1 * | 6/2007 | Angibaud | 623/20.14 |
| 2007/0179628 | A1 * | 8/2007 | Rochetin | 623/20.34 |
| 2008/0004708 | A1 * | 1/2008 | Wyss | 623/20.24 |
| 2008/0300690 | A1 * | 12/2008 | Burstein et al. | 623/20.29 |
| 2009/0082873 | A1 * | 3/2009 | Hazebrouck et al. | 623/20.32 |
| 2009/0125114 | A1 | 5/2009 | May et al. | |
| 2009/0125115 | A1 | 5/2009 | Popoola et al. | |
| 2009/0149964 | A1 * | 6/2009 | May et al. | 623/20.15 |
| 2009/0299482 | A1 * | 12/2009 | Metzger et al. | 623/20.29 |
| 2010/0016978 | A1 * | 1/2010 | Williams et al. | 623/20.27 |
| 2010/0100189 | A1 | 4/2010 | Metzger | |
| 2010/0100190 | A1 | 4/2010 | May et al. | |
| 2010/0222890 | A1 | 9/2010 | Barnett et al. | |
| 2011/0202139 | A1 | 8/2011 | Metzger et al. | |
| 2011/0251694 | A1 * | 10/2011 | Wasielewski | 623/19.11 |
| 2011/0251695 | A1 | 10/2011 | Lenz et al. | |
| 2012/0035737 | A1 | 2/2012 | Sanford et al. | |
| 2012/0158152 | A1 | 6/2012 | Claypool et al. | |
| 2012/0265316 | A1 | 10/2012 | Metzger et al. | |
| 2012/0296438 | A1 * | 11/2012 | Metzger et al. | 623/20.29 |
| 2013/0184831 | A1 * | 7/2013 | McMinn | 623/20.35 |
| 2013/0190883 | A1 * | 7/2013 | Collard et al. | 623/20.29 |
| 2014/0018929 | A1 * | 1/2014 | Heggendorn et al. | 623/20.27 |
| 2014/0114427 | A1 * | 4/2014 | Metzger | 623/20.33 |
| 2014/0156015 | A1 * | 6/2014 | Parisi et al. | 623/20.29 |
| 2014/0277534 | A1 * | 9/2014 | Wasielewski | 623/20.27 |
| 2014/0277535 | A1 * | 9/2014 | Metzger et al. | 623/20.29 |

OTHER PUBLICATIONS

"U.S. Appl. No. 13/162,789, Notice of Allowance mailed Aug. 21, 2013", 8 pgs.

"U.S. Appl. No. 13/162,789, Response filed Jan. 3, 2013 to Restriction Requirement mailed Dec. 7, 2012", 1 pg.

"U.S. Appl. No. 13/162,789, Response filed May 22, 2013 to Non Final Office Action mailed Feb. 22, 2013", 8 pgs.

"U.S. Appl. No. 13/162,789, Restriction Requirement mailed Dec. 7, 2012", 5 pgs.

* cited by examiner

REVISION KNEE TIBIAL LOCKING MECHANISM

CROSS-REFERENCE TO RELATED APPLICATIONS

This application is a divisional application of U.S. patent application Ser. No. 13/162,789 filed on Jun. 17, 2011, which issued as U.S. Pat. No. 8,617,250 on Dec. 31, 2013. The entire disclosure of application Ser. No. 13/162,789 is incorporated herein by reference.

FIELD

The present disclosure relates to knee joint prosthesis and, more particularly, to a tibial prosthesis assembly having a tibial insert that is permitted to rotate a predetermined amount around a superior surface of a tibial component.

BACKGROUND

This section provides background information related to the present disclosure which is not necessarily prior art.

A knee joint prosthesis typically comprises a femoral component and a tibial component. The femoral component and the tibial component are designed to be surgically attached to the distal end of the femur and the proximal end of the tibia, respectively. The femoral component is further designed to cooperate with the tibial component in simulating the articulating motion of an anatomical knee joint. Such knee joint prostheses are generally referred to as primary knee prostheses. Knee joint prostheses, in combination with ligaments and muscles, attempt to duplicate natural knee motion as well as absorb and control forces generated during the range of flexion. In some instances however, it may be necessary to replace an existing prosthesis. Such replacement prostheses are generally referred to as revision knee prostheses. Some knee joint prostheses incorporate a tibial insert or bearing that is fixed relative to the tibial component. Such a configuration may have a very constrained tibiofemoral articulation in axial rotation. During surgery, the tibial component may be rotationally aligned with tibial landmarks. Similarly, the femoral component may be rotationally aligned with femoral landmarks. Therefore, the tibial and femoral components may be positioned independently of each other. Because they are positioned independently, the femoral component and the tibial component may not optimally align with each other. In this regard, when highly constrained articulations are forced to mate, the constrained bearing and the bone/implant interface may experience undesirable higher stresses.

SUMMARY

This section provides a general summary of the disclosure, and is not a comprehensive disclosure of its full scope or all of its features.

The present teachings provide for a tibial prosthesis assembly including a tibial component and a tibial insert. The tibial component includes an inferior bone engaging surface, a superior surface, and a first retention feature. The tibial insert includes an inferior tibial component engaging surface, a superior bearing surface, and a second retaining feature. The first and the second retaining features cooperate to mate the tibial insert with the tibial component at one of a plurality of fixed rotational orientations relative to the tibial component.

The present teachings further provide for a tibial prosthesis assembly including a tibial tray and a tibial insert. The tibial tray includes an inferior bone engaging surface, a superior surface, and a first retaining feature including a first indexable member. The tibial insert has an inferior tray engaging surface, a superior bearing surface, and a second retaining feature including a second indexable member. The second indexable member of the tibial insert is configured to indexably mate with the first indexable member of the tibial tray at one of a plurality of fixed rotational orientations relative to the tibial tray in an assembled position.

The present teachings also provide for a tibial prosthesis assembly including a tibial component and a tibial insert. The tibial component includes a tibial tray and a first stem extending therefrom. The tibial tray includes a superior bearing engaging surface and an inferior bone engaging surface. The tibial component defines a first retention member extending from the superior bearing engaging surface into the first stem. The tibial insert includes an inferior tray engaging surface, a superior bearing surface, and a second stem extending from the inferior tray engaging surface. The second stem includes a second retention member configured to be received within, and cooperate with, the first retention member to indexably mate with the first retention member.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

The following description of the embodiments is specifically directed toward a tibial prosthesis having a tibial insert that incorporates a superiorly extending stabilizing post. It will be appreciated by those skilled in the art that the present disclosure is clearly not limited to tibial prostheses incorporating tibial inserts having such a geometry. Furthermore, it will be appreciated that the tibial prosthesis assembly may be used as part of a revision or a primary knee joint procedure.

Figure 1:
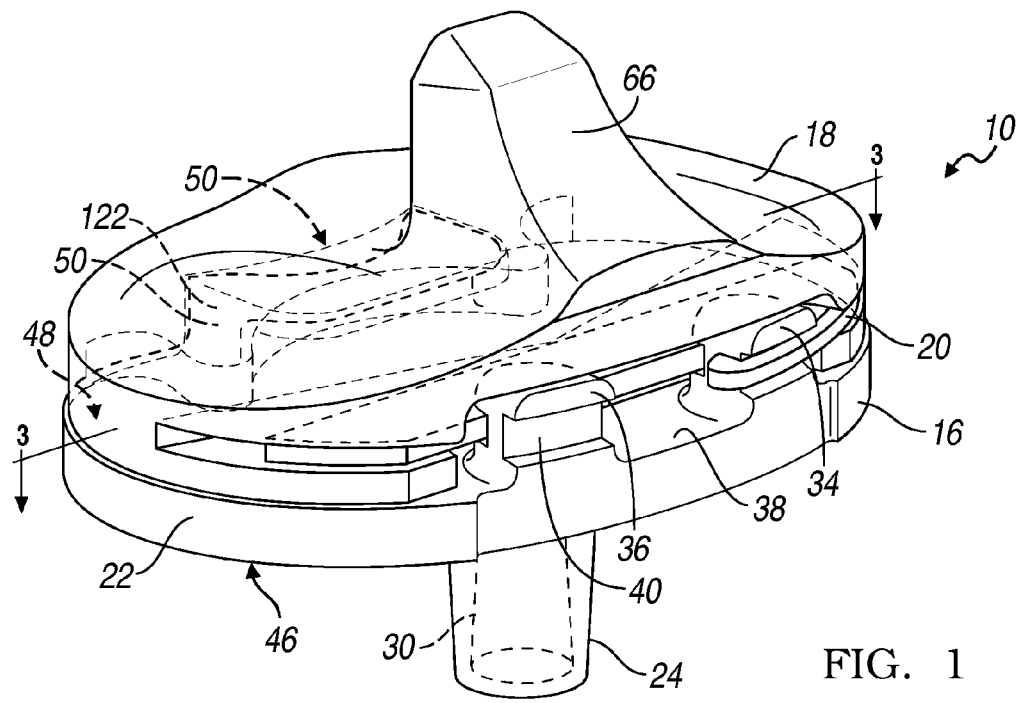
FIG. 1 is an anterior perspective view of a tibial prosthesis assembly constructed in accordance to one example of the present teachings and including a tibial component, a tibial insert, and a locking bar.
Figure 5:
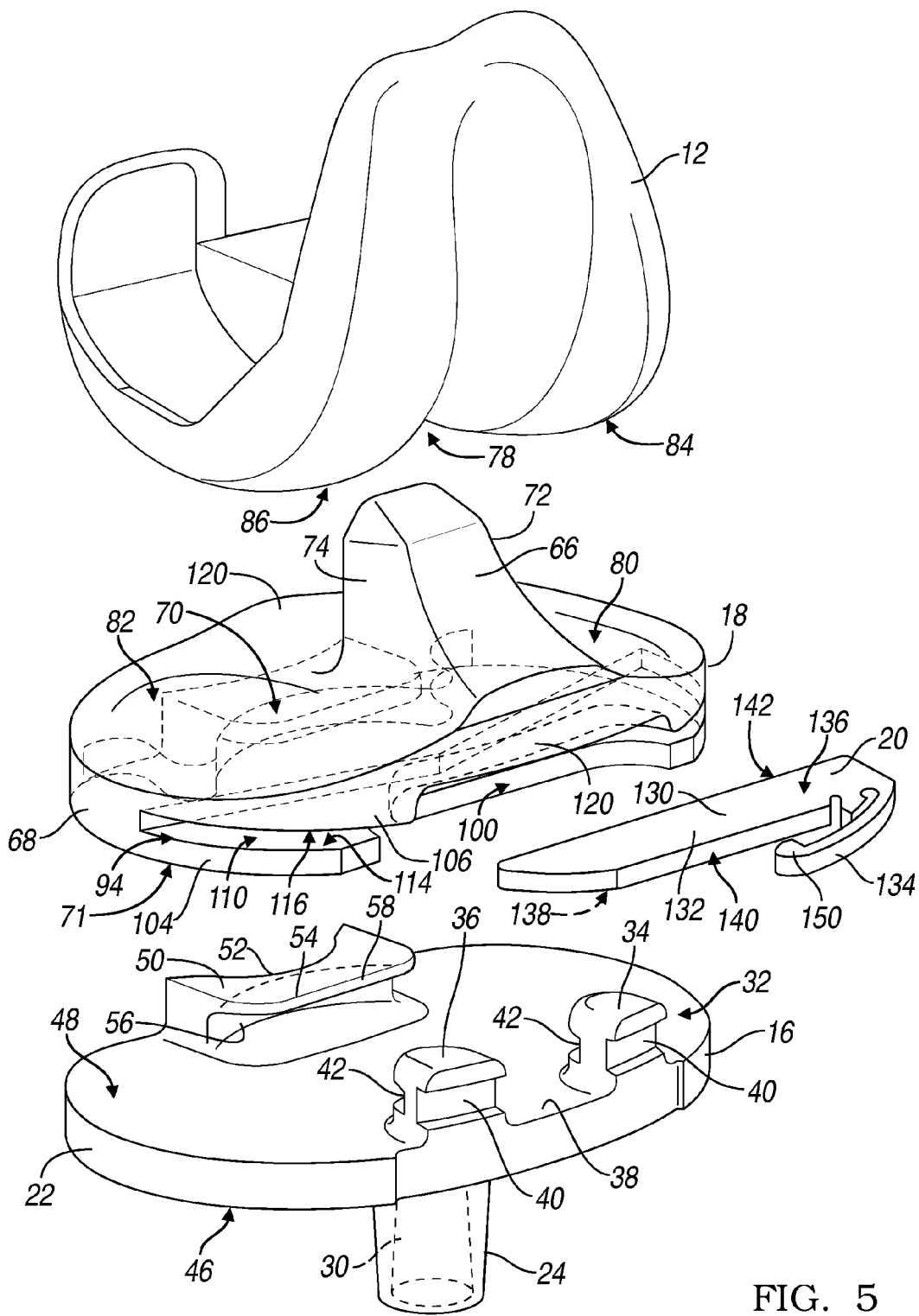
FIG. 5 is an exploded anterior perspective view of the tibial prosthesis assembly of FIG. 1.

With initial reference now to FIGS. 1 and 5, a tibial prosthesis assembly constructed in accordance to one example of the present teachings is shown and generally identified at reference numeral 10. The tibial prosthesis assembly 10 is adapted to be secured to the proximal end of a tibia after the tibia has been resected in a manner well-known in the art. Furthermore, the tibial prosthesis assembly 10 can be configured to cooperate with a complementary femoral component 12 that may be secured to the distal end of the femur after the femur has been resected in a manner which is well-known in the art.

The tibial prosthesis assembly 10 can generally include a tibial component 16, a tibial insert 18, and a locking bar 20. The tibial component 16 can include a platform-like tibial tray 22 and an inferiorly extending tibial stem 24. The tibial stem 24 is configured to be received in a corresponding opening (not shown) made by the surgeon in the longitudinal center of the tibia. A bore 30 may be disposed within the tibial stem 24 that is configured to receive a suitable support member (such as an offset stem adapter or stem extension) that may be secured to the tibia in a manner well-known in the art. The tibial tray 22 may be formed of titanium or other suitable biocompatible material and may be constructed of different sizes having an overall medial-lateral dimension ranging from 59 mm to 91 mm. Other dimensions are contemplated.

The tibial tray 22 can further a further retaining feature 32 including a pair of integrally formed posts 34 and 36 which extend superiorly at an anterior edge 38 of the tibial tray 22. The posts 34 and 36 may be positioned equally spaced from either side of the center of the tibial component 16 in the sagittal plane. The anterior surface of each of the posts 34 and 36 includes an anterior horizontal groove 40. The posterior surface of each of the posts 34 and 36 can include a posterior horizontal groove 42. The anterior horizontal groove 40 and the posterior horizontal groove 42 cooperate to receive the locking bar 20 which is able to secure the tibial insert 18 from substantial liftoff from the tibial tray 22 while permitting a predetermined amount of rotation of the tibial insert 18 around the tibial tray 22 as will be described more fully herein.

Figure 3:
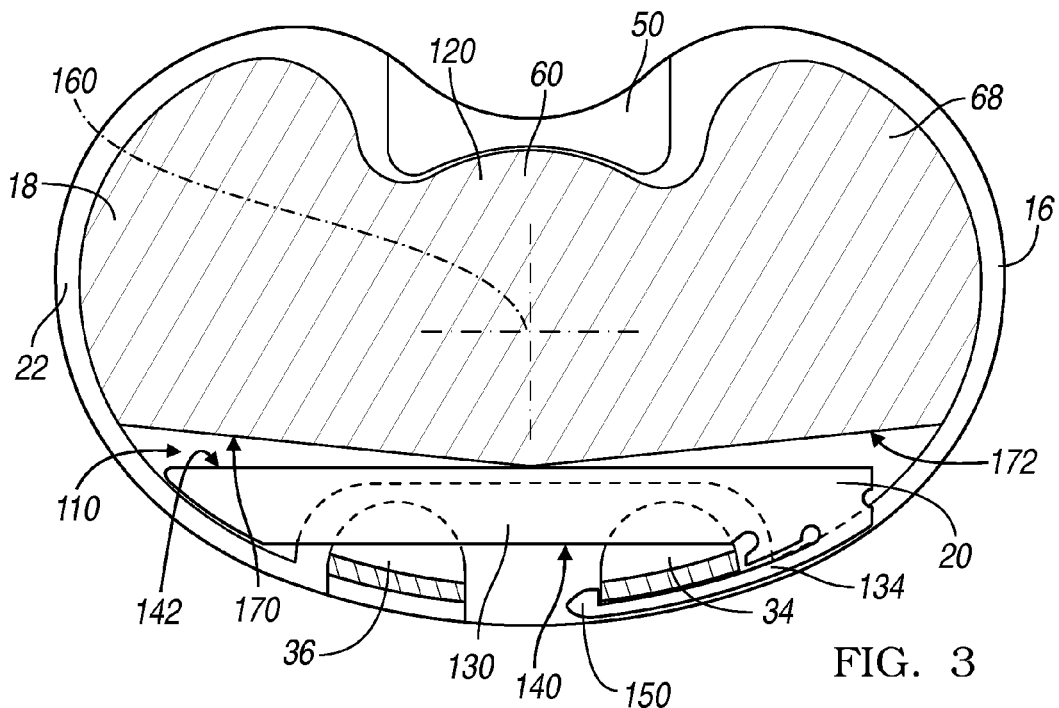
FIG. 3 is a cross-sectional view of the tibial prosthesis assembly taken along lines 3-3 of FIG. 1.
Figure 4:
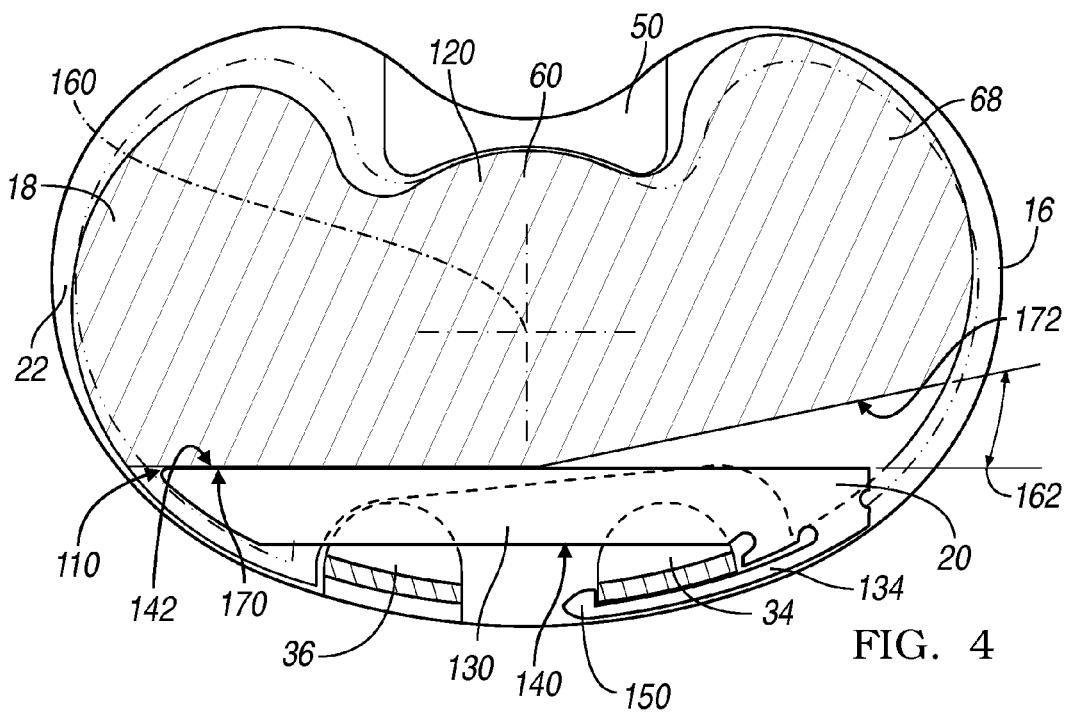
FIG. 4 is a cross-sectional superior view of the tibial prosthesis assembly of FIG. 3 and shown with the tibial insert rotated relative to the tibial component.

The tibial tray 22 can further include an inferior bone engaging surface 46 and a superior insert engaging surface 48. Disposed on the superior surface 48 of the tibial tray 22 can be a unitarily formed posterior projection 50. The posterior projection 50 can be formed as part of the first retaining feature as will become appreciated. The posterior projection 50 can extend superiorly from a posterior portion of the tibial tray 22. The posterior projection 50 can have a posterior side 52 which conforms with a corresponding posterior edge of the tibial tray 22 and an anterior side 54 which has a horizontal channel 56 formed generally between an overhang 58 of the posterior projection 50 and the superior surface 48 of the tibial tray 22. As will become appreciated herein, the horizontal channel 56 can be used to engage a horizontal flange 60 (FIGS. 3 and 6) formed in the tibial insert 18 in a manner described more fully below.

With particular reference now to FIGS. 1-5, the tibial insert 18 will be described in greater detail. The tibial insert 18 may be symmetrical about the sagittal plane in one example thereby permitting the tibial insert 18 to be used with femoral components which are designed either for the left or the right knee. In the exemplary tibial insert 18, a stabilizing post projects superiorly from a tibial insert body 68. The tibial insert body can have a superior surface 70 and an inferior tray engaging surface 71. The stabilizing post 66 can extend superiorly from the superior surface 70 of the tibial insert 18 and can include a first and a second laterally-spaced apart sides 72 and 74. The laterally-spaced apart sides 72 and 74 of the stabilizing post 66 can be positioned so as to extend into an intercondylar recess 78 (FIG. 5) of the femoral component 12. Other configurations are contemplated.

Disposed on the superior surface 70 of the tibial insert 18 may be a first tibial bearing surface 80 and a second tibial bearing surface 82. The first and second tibial bearing surfaces 80 and 82 may be dish-shaped in configuration. In this regard, the first and second tibial bearing surfaces 80 and 82 may each be concavely curved in the coronal plane in a manner substantially similar to first and second femoral bearing surfaces 84 and 86 of the femoral component 12.

Figure 2:
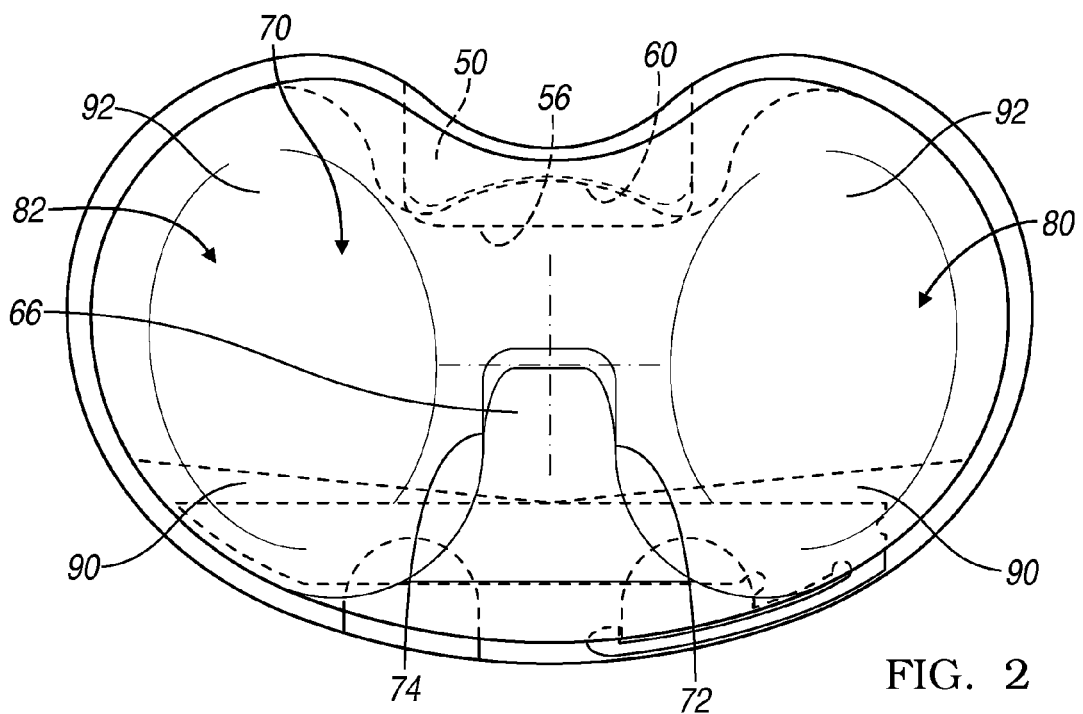
FIG. 2 is a superior view of the tibial prosthesis assembly of FIG. 1.

With particular reference now to FIG. 2, additional features of the tibial insert 18 will be described. The first and second tibial bearing surfaces 80 and 82 can each further include a first and second articulating surfaces 90 and 92. The first and second articulating surfaces 90 and 92 can be used to limit dislocation of the femoral component 12 in the sagittal plane with respect to the tibial component 16 and may be located at the anterior and posterior portions of each of the first and second tibial bearing surfaces 80 and 82. Both the articulating surfaces 90 and 92 may be concavely curved in the superior direction in the sagittal plane.

With reference now to FIGS. 1-6, the tibial insert 18 can further include a second retaining feature 94. The second retaining feature 94 can include vertical anterior recess 100 located on an anterior portion 102 of the tibial insert 18. The vertical anterior recess 100 can be configured to receive the posts 34 and 36 of the tibial tray 22. In addition, the anterior portion 102 of the tibial insert 18 can further include an inferior ledge 104 and a superior ledge 106 that cooperatively define a horizontal groove 110 therebetween. More specifically, the inferior ledge 104 has a first or upper surface 114 that opposes a second or lower surface 116 of the superior ledge 106.

The tibial insert body 68 further includes a posterior portion 120 that has a horizontal posterior recess 122 (FIG. 6) that may be adapted to receive the posterior projection 50 of the tibial tray 22 as shown in FIG. 1. The horizontal posterior recess 122 can also be formed as part of the second retaining feature 94 as will become appreciated. The horizontal posterior recess 122 incorporates the horizontal flange 60 (FIGS. 3 and 6) which is adapted to be received in the horizontal channel 56 formed in the posterior projection 50.

The locking bar 20 will now be further described. The locking bar 20 can generally comprise a main body 130 having an insertion portion 132 and a retaining portion 134. The insertion portion 132 can generally provide a first or upper surface 136 and a second or lower surface 138. The main body 130 can further include an anterior-facing surface 140 and a posterior-facing surface 142. The retaining portion 134 can further include a lobe 150 formed on a terminal end.

Figure 6:
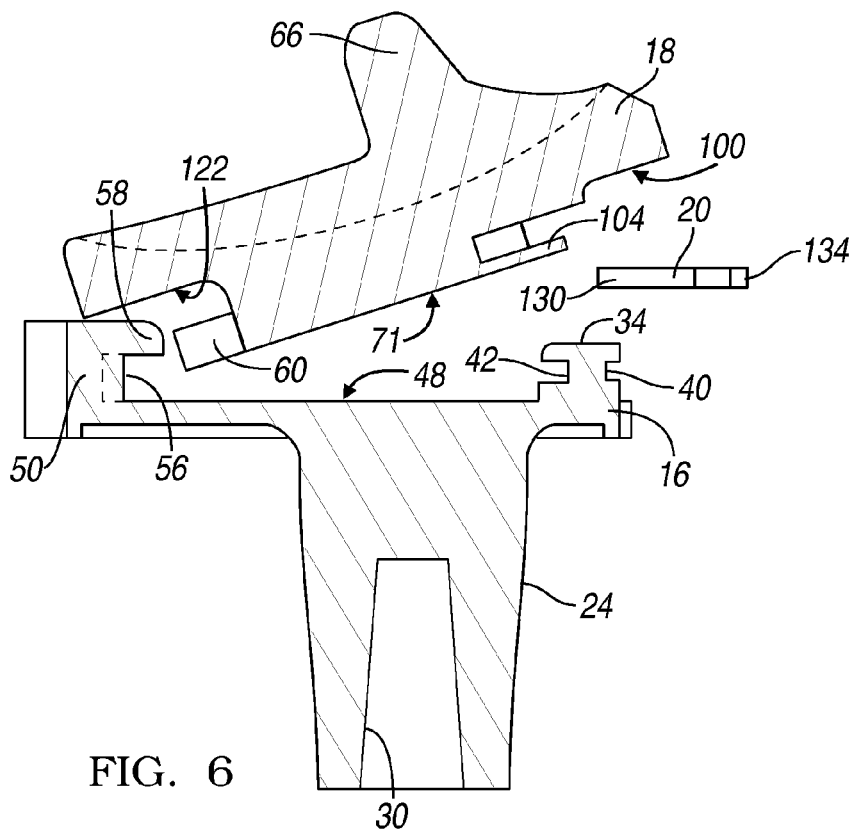
FIG. 6 is a cross-sectional view of the tibial prosthesis assembly of FIG. 5 taken along a sagittal plane and shown with the tibial insert initially positioned toward the tibial component during an assembly step.
Figure 7:
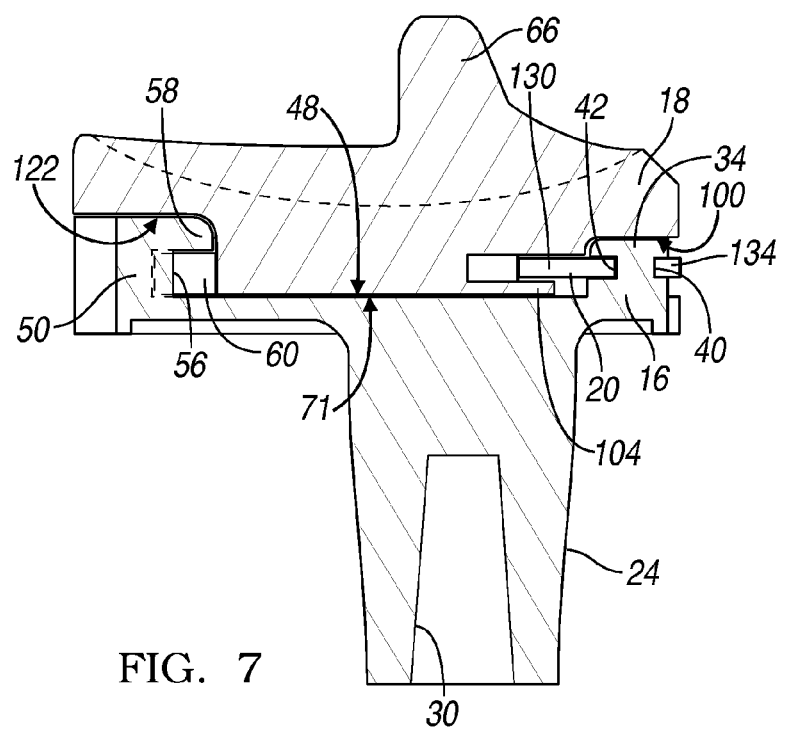
FIG. 7 is a cross-sectional view of the tibial prosthesis assembly of FIG. 6 shown subsequent to installation of the locking bar.

Assembling the tibial insert 18 to the tibial tray 22 according to one example of the present teachings will now be described. Initially, a surgeon can advance the tibial insert 18 toward the superior surface 48 of the tibial tray 22 as illustrated in FIG. 6. The horizontal flange 60 of the tibial insert body 68 can then be located generally under the overhang 58 of the posterior projection 50 such that the horizontal flange 60 locates generally into the horizontal channel 56 on the posterior projection 50 of the tibial tray 22. Next, the surgeon can generally rotate the tibial insert 18 anteriorly to the position illustrated in FIG. 7. Next, the surgeon can advance the locking bar 20 into the horizontal groove 110 of the tibial insert 18 as well as the horizontal posterior grooves 42 formed on the first and second posts 34 and 36. The locking bar 20 can be further advanced until the lobe 150 generally wraps around the post 34 as illustrated in FIG. 1. It will be appreciated that while the locking bar 20 is shown with the lobe 150 wrapped around the post 34, the locking bar 20 may alternatively be inserted from the other direction when the lobe 150 wraps around the post 36. Notably, at this time, the inferior ledge 104 of the tibial insert 18 is confined between the locking bar 20 and the superior surface 48 of the tibial tray 22 precluding substantial lift-off of the tibial insert 18 from the tibial tray 22. The tibial insert 18 however, is permitted to rotate around an axis 160 (FIG. 3) to a predetermined angle of rotation 162 (counter-clockwise, as viewed in FIG. 4, or alternatively clockwise, not specifically shown). Explained further, the tibial insert body 68 includes a first bearing rotation stop surface 170 and a second bearing rotation stop surface 172 formed at a generally posterior most end of the horizontal groove 110. The stop surfaces 170 and 172 can define an angle less than 180 degrees relative to each other.

The tibial insert 18 is free to rotate around the axis 160 until either the first bearing rotation stop surface 170 or the second bearing rotation stop surface 172 engages the posteriorly facing surface 142 of the locking bar 20. Other configurations are contemplated. For example, various tibial insert bodies 68 can be provided that have unique stop surfaces 170 and 172 that define various angles. Additionally or alternatively, various locking bars 20 can be provided that have posteriorly facing surfaces 142 that attain various opposing geometries relative to the stop surfaces 170 and 172. For example, some posterior facing surfaces 142 may have an angle less than 180 degrees. In this regard, a surgeon may intraoperatively select a tibial insert body 68 and/or a locking bar 20 that cooperate to provide a desired fixed amount of rotation of the insert 18 relative to the tibial component 16. The insert 18 therefore can be selectively indexable to a plurality of fixed (or mobile) positions or orientations relative to the tibial component 16. Again, it will be appreciated that the tibial insert 18 is inhibited from lift-off from the tibial tray 22 as the main body 130 of the locking bar 20 precludes superior advancement of the tibial insert 18 by blocking the inferior ledge 104 from superior advancement. Concurrently, the horizontal flange 60 of the tibial insert 18 can also be restricted from lift-off by the overhang 58 provided on the posterior projection 50 of the tibial tray 22. Those skilled in the art will appreciate that other configurations are contemplated where use of a locking bar 20 is not necessary. In this regard, structure on the first and second retaining members 32 and 94 may cooperate to restrict the tibial insert 18 from lift-off while permitting a predetermined amount of rotation around the axis 160.

Figure 8:
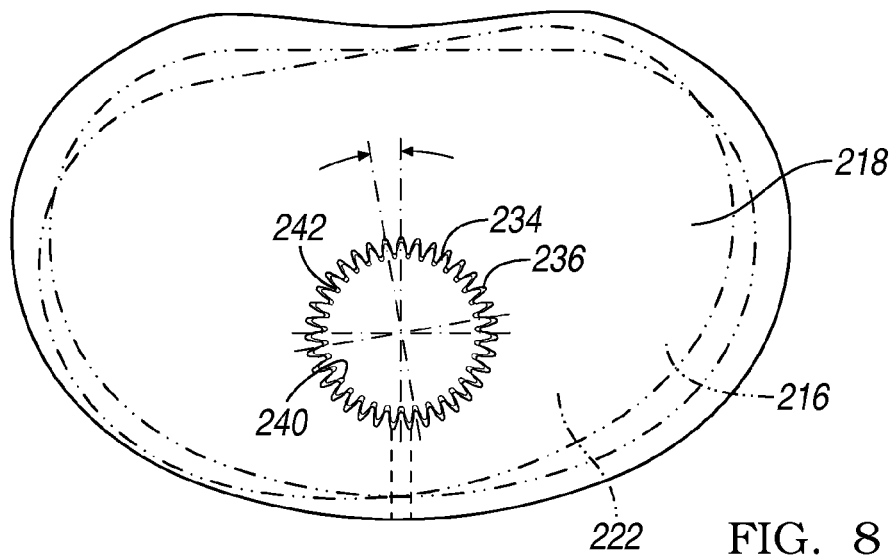
FIG. 8 is a superior view of a tibial prosthesis assembly constructed in accordance to additional features of the present teachings.
Figure 9:
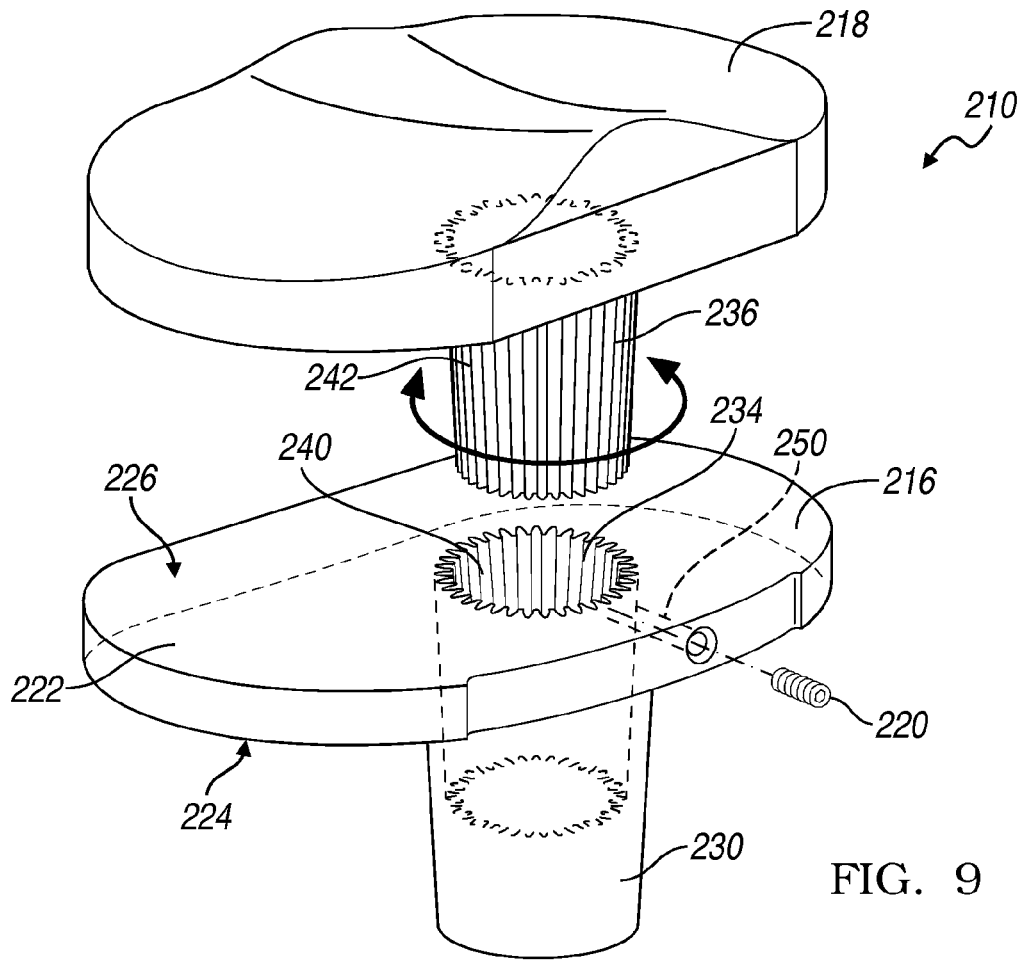
FIG. 9 is an exploded anterior perspective view of the tibial prosthesis assembly of FIG. 8.

Turning now to FIGS. 8 and 9, a tibial prosthesis assembly 210 constructed in accordance to additional features of the present teachings will be described. The tibial prosthesis assembly 210 can generally include a tibial component 216 and a tibial insert 218. The tibial prosthesis assembly 210 can optimally include a set screw 220. The tibial component 216 can generally include a platform-like tibial tray 222 having an inferior bone engaging surface 224 and a superior bearing engaging surface 226. A stem 230 can generally extend inferiorly from the tray 222. The tibial component 216 includes a first retaining or interlock feature 234 that is configured to rotatably lock with a second retaining or interlock feature 236 formed on the tibial insert 218. In the example shown, the first interlock feature 234 is in the form of female splines 240 that rotatably mesh with cooperatively formed male splines 242 formed on the second interlock feature 236 of the tibial insert 218. As can be appreciated, during assembly, a surgeon may index the second interlock feature 236 to a desired rotational orientation relative to the first interlock feature 234 and then advance the male splines 242 inferiorly into meshing engagement with the female splines 240 of the first interlock feature 234. Then, a surgeon may advance the set screw 220 through a passage 250 defined through the tibial tray 222. The set screw 220 can engage the male splines 242 and inhibit the second interlock feature 236 from lifting out of the first interlock feature 234.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A tibial prosthesis assembly comprising:
 a tibial component including an inferior bone engaging surface, a superior surface, a side surface joining the inferior bone engaging surface and the superior surface to define a perimeter, a first stem extending from the inferior bone engaging surface, and a first retention feature including a receptacle defined by the tibial component and extending into the first stem, the receptacle including a plurality of first splines extending into the first stem and arranged directly adjacent to one another about an entirety of the receptacle; and
 a tibial insert including an inferior tibial component engaging surface, a superior bearing surface, an outer portion joining the inferior tibial component engaging surface and the superior bearing surface, a second stem extending from the inferior tibial component engaging surface, and a second retaining feature including a plurality of second splines directly adjacent to one another and extending along a length of the second stem about an entirety of an outer surface of the second stem;
 wherein the plurality of second splines are configured to indexably mate with the plurality of first splines;
 wherein the first and the second retaining features cooperate to mate the tibial insert with the tibial component at one of a plurality of fixed rotational orientations relative to the tibial component; and
 wherein the plurality of fixed rotational orientations includes multiple orientations where the outer portion remains fully within the perimeter.

2. The tibial prosthesis assembly of claim 1, wherein a opening of the receptacle is defined by the superior surface of the tibial component.

3. The tibial prosthesis assembly of claim 2, wherein the first retention feature extends through a tibial tray of the tibial component.

4. The tibial prosthesis assembly of claim 1, wherein the tibial component defines a passage configured to receive a fastener therethrough to secure the second retaining feature within the first retaining feature.

5. The tibial prosthesis assembly of claim 4, wherein the fastener includes a set screw.

6. The tibial prosthesis assembly of claim 1, wherein:
the plurality of first splines extend into the first stem along a length of the receptacle below the inferior bone engaging surface; and
the plurality of second splines extend along an entire length of the outer surface of the second stem.

7. A tibial prosthesis assembly comprising:
a tibial tray having an inferior bone engaging surface, a superior surface, a side surface joining the inferior bone engaging surface and the superior surface to define a perimeter, a first stem extending from the inferior bone engaging surface, and a first retaining feature including a receptacle defined by the tibial component and extending into the first stem, the receptacle including a first indexable member extending into the first stem and about an entirety of the receptacle; and
a tibial insert having an inferior tray engaging surface, a superior bearing surface, an outer portion joining the inferior tray engaging surface and the superior bearing surface, a second stem extending from the inferior tray engaging surface, and a second retaining feature including a second indexable member extending along a length of the second stem about an entirety of an outer surface of the second stem;
wherein the second indexable member of the tibial insert is configured to indexably mate with the first indexable member of the tibial tray at one of a plurality of fixed rotational orientations relative to the tibial tray in an assembled position, wherein the plurality of fixed rotational orientations includes multiple orientations where the outer portion remains fully within the perimeter.

8. The tibial prosthesis assembly of claim 7, wherein the first indexable member includes one of a female splined portion and a male splined portion, and the second indexable member includes the other of the female splinted portion and male splined portion.

9. The tibial prosthesis assembly of claim 8, wherein the tibial tray defines a passage that connects an outer surface of the tibial tray with the female splined portion.

10. The tibial prosthesis assembly of claim 9, further comprising a set screw, the set screw is selectively advanced through the passage and into engagement with the second indexable member to secure the second retaining feature within the first retaining feature.

11. The tibial prosthesis assembly of claim 8, wherein:
the first indexable member extends into the first stem along a length of the receptacle below the inferior bone engaging surface; and
the second indexable member extends along an entire length of the outer surface of the second stem.

12. A tibial prosthesis assembly comprising:
a tibial component including a tibial tray and a first stem extending therefrom, the tibial tray including a superior bearing engaging surface, an inferior bone engaging surface from which the first stem extends, and a side surface joining the inferior bone engaging surface and the superior bearing engaging surface to define a perimeter, the tibial component defines a first retention member including a receptacle extending from the superior bearing engaging surface into the first stem, the first retention member includes one of female splines or male splines defined by the receptacle to be adjacent to one another about an entirety of a circumference of the receptacle and to extend into the first stem along a length of the receptacle below the inferior bone engaging surface; and
a tibial insert including an interior tray engaging surface, a superior bearing surface, an outer portion joining the inferior tray engaging surface and the superior bearing surface, and a second stem extending from the inferior tray engaging surface, the second stem includes a second retention member configured to be received within, and cooperate with, the first retention member to indexably mate with the first retention member at one of a plurality of fixed rotational orientations relative to the tibial tray in an assembled position, the second retention member includes the other of the female splines or the male splines directly adjacent to one another and extending along an entire length of the second stem about an entirety of an outer surface of the second stem;
wherein the plurality of fixed rotational orientations includes multiple orientations where the outer portion remains fully within the perimeter.

13. The tibial prosthesis assembly of claim 12, wherein the tibial tray defines a passage extending from the first retention member to an exterior side surface of the tibial tray.

14. The tibial prosthesis assembly of claim 13, wherein the passage is configured to receive a fastener therethrough to contact the second stem and retain the second stem within the first stem.

15. The tibial prosthesis assembly of claim 14, wherein the passage extends perpendicular to the first stem.

16. The tibial prosthesis assembly of claim 15, wherein the fastener is a set screw.

* * * * *